(12) United States Patent
Lozano

(10) Patent No.: US 8,195,298 B2
(45) Date of Patent: Jun. 5, 2012

(54) METHOD FOR TREATING NEUROLOGICAL/PSYCHIATRIC DISORDERS WITH STIMULATION TO THE SUBCAUDATE AREA OF THE BRAIN

(76) Inventor: Andres M Lozano, Toronto (CA)

( * ) Notice: Subject to any disclaimer, the term of this patent is extended or adjusted under 35 U.S.C. 154(b) by 209 days.

(21) Appl. No.: 12/320,870

(22) Filed: Feb. 6, 2009

(65) Prior Publication Data

US 2009/0210018 A1 Aug. 20, 2009

Related U.S. Application Data

(60) Provisional application No. 61/064,093, filed on Feb. 15, 2008.

(51) Int. Cl.
*A61N 1/18* (2006.01)
(52) U.S. Cl. .............................. 607/45; 607/3
(58) Field of Classification Search .................. 607/45
See application file for complete search history.

(56) References Cited

U.S. PATENT DOCUMENTS

| | | | |
|---|---|---|---|
| 4,692,147 A | 9/1987 | Duggan | |
| 5,188,104 A | 2/1993 | Wernicke et al. | |
| 5,193,539 A | 3/1993 | Schulman et al. | |
| 5,193,540 A | 3/1993 | Schulman et al. | |
| 5,263,480 A | 11/1993 | Wernicke et al. | |
| 5,312,439 A | 5/1994 | Loeb | |
| 5,324,316 A | 6/1994 | Schulman et al. | |
| 5,405,367 A | 4/1995 | Schulman et al. | |
| 5,752,911 A | 5/1998 | Canedo et al. | |
| 5,782,798 A | 7/1998 | Rise | |
| 6,051,017 A | 4/2000 | Loeb et al. | |
| 6,128,537 A | 10/2000 | Rise | |
| 6,132,361 A | 10/2000 | Epstein et al. | |
| 6,263,237 B1 * | 7/2001 | Rise | 607/3 |
| 6,425,852 B1 | 7/2002 | Epstein et al. | |
| 6,567,696 B2 | 5/2003 | Voznesensky et al. | |
| 6,592,509 B1 | 7/2003 | Hunter, Jr. | |
| 6,735,474 B1 | 5/2004 | Loeb et al. | |
| 6,735,475 B1 | 5/2004 | Whitehurst et al. | |
| 6,782,292 B2 | 8/2004 | Whitehurst | |
| 6,871,098 B2 | 3/2005 | Nuttin, et al. | |
| 6,950,707 B2 | 9/2005 | Whitehurst | |

(Continued)

FOREIGN PATENT DOCUMENTS

| | | |
|---|---|---|
| CA | 2432810 A1 | 12/2004 |
| WO | WO-98/37926 | 9/1998 |
| WO | WO-98/43700 | 10/1998 |
| WO | WO 98/43701 | 10/1998 |

(Continued)

OTHER PUBLICATIONS

Cosgrove, G. Rees et al. "Psychosurgery." Massachusetts General Hospital. May 11, 2005. Dec. 29, 2010. <http://neurosurgery.mgh.harvard.edu/functional/psysurg.htm>.*

(Continued)

*Primary Examiner* — Carl H Layno
*Assistant Examiner* — Allen Porter, Jr.
(74) *Attorney, Agent, or Firm* — Christopher S. L. Crawford; Craig Hoersten; Peter R. Lando

(57) ABSTRACT

A method for treating a patient with a neurological or psychiatric disorder, comprising applying stimulation to at least a portion of the patient's subcaudate white matter of the subcaudate area under conditions effective to provide the patient with at least a partial relief from the neurological or psychiatric disorder. The stimulation may be electrical and/or pharmacological.

15 Claims, 3 Drawing Sheets

U.S. PATENT DOCUMENTS

| | | | | |
|---|---|---|---|---|
| 2004/0073273 | A1* | 4/2004 | Gluckman et al. | 607/48 |
| 2005/0033379 | A1* | 2/2005 | Lozano et al. | 607/45 |
| 2005/0065574 | A1* | 3/2005 | Rezai | 607/45 |
| 2005/0177192 | A1* | 8/2005 | Rezai et al. | 607/3 |
| 2005/0240242 | A1* | 10/2005 | DiLorenzo | 607/45 |
| 2006/0100671 | A1* | 5/2006 | Ridder | 607/45 |
| 2007/0005115 | A1* | 1/2007 | Lozano et al. | 607/45 |
| 2007/0038264 | A1* | 2/2007 | Jaax et al. | 607/45 |
| 2007/0100392 | A1* | 5/2007 | Maschino et al. | 607/45 |
| 2008/0288018 | A1* | 11/2008 | Rezai et al. | 607/45 |

OTHER PUBLICATIONS

Cosgrove, G.R., "Cingulotomy for Depression and OCD," Springer-Verlag, Berlin/Heidelberg, 2009, pp. 2887-2896.

Greenberg, Benjamin D., et al., "Current Status of Deep Brain Stimulation," Primary Psychiatry, Oct. 2005: 12(10): 59-64.

Tye, Susannah J., et al., "Disrupting Disordered Neurocircuitry: Treating Refractory Psychiatric Illness with Neuromodulation," Mayo Clinic Proceedings, Jun. 2009, vol. 84, No. 6, pp. 522-532.

* cited by examiner

METHOD FOR TREATING NEUROLOGICAL/PSYCHIATRIC DISORDERS WITH STIMULATION TO THE SUBCAUDATE AREA OF THE BRAIN

FIELD OF THE INVENTION

The present invention relates to the treatment of neurological/psychiatric disorders. More specifically, the present invention is directed to the treatment of such disorders by the use of nerve tissue stimulation and/or pharmacological infusion to the white matter pathways which lie ventral to the caudate nucleus and striatum of the brain to treat the neurological/psychiatric disorder.

BACKGROUND OF THE INVENTION

Permanent surgically induced lesions in the subcaudate area which encompasses a large assembly of axonal projections have been used to treat a number of neurological and psychiatric disorders. Although these procedures have sometimes been effective, they were often associated with serious complications including decreased motivation and loss of interest as well as some neuropsychological disorders and cognitive disturbances.

Deep brain stimulation or the infusion of drugs into the brain has been conducted to modulate the neural activity in disease affected circuitry and improve neurological and psychiatric function while avoiding the cost of irreversible side effects. The use of deep brain stimulation is taught for example in U.S. Pat. No. 5,188,104, U.S. Pat. No. 5,263,480, U.S. Pat. No. 5,782,798, U.S. Pat. No. 6,128,537 and U.S. Pat. No. 6,871,098 and U.S. Pat. No. 6,950,707 (the disclosures of which are incorporated herein by reference in their entirety) for treating certain brain areas and disorders.

While the prior art has used deep brain stimulation, it is desirable to use such stimulation for the treatment of neurological and psychiatric disorders manifested by abnormal neural activity in regions receiving inputs or relaying outputs through the subcaudate area of the brain. This has not been previously demonstrated and therefore there remains a need to try and treat such disorders where tracks in the subcaudate region are abnormally affected.

SUMMARY OF THE INVENTION

According to an aspect of the present invention there is provided a method for the treatment of neurological/psychiatric disorders in a patient, the method comprising administration of stimulation to the subcaudate area of said patient for a time, duration and frequency to decrease or substantially ameliorate the neurological/psychiatric disorder.

In aspects of the invention, the neurological/psychiatric disorder is schizophrenia or depression.

According to another aspect of the present invention is a method for modulating brain subcaudate white matter tissue to treat depression and/or schizophrenia, the method comprising: placing at least a first lead having at least a first proximal electrode and at least a first distal electrode in a subcaudate white matter portion of the brain; connecting the first lead to a neurological stimulator; configuring the first proximal electrode and the first distal electrode in a manner to deliver a stimulation signal; delivering the stimulation signal to the first proximal electrode and the first distal electrode; and, modulating neural activity in the subcaudate white matter tissue.

In embodiments of the invention, the method and therapeutic system comprise a surgically implanted device in communication with an area of the subcaudate area of the brain. The device or stimulation system is operated to stimulate the predetermined site thereby treating the eating neurological/psychiatric disorder, i.e. the various underlying aspects thereof. The device can include a stimulation portion or a probe, for example, an electrode, an electrode assembly (e.g., electrical stimulation lead), pharmaceutical-delivery assembly (e.g., catheters) or combinations of these and/or a signal generator or signal source or pulse generating source (i.e. (i.e., electrical signal source, chemical signal source (i.e., pharmaceutical delivery pump) or magnetic signal source). The probe may be coupled to the signal source, pharmaceutical delivery pump, or both which, in turn, is operated to stimulate the predetermined treatment site. Yet further, the probe and the signal generator or source can be incorporated together, wherein the signal generator and probe are formed into a unitary or single unit, such unit may comprise, one, two or more electrodes. These devices are known in the art as microstimulators, for example, Bion™ manufactured by Advanced Bionics Corporation.

In further embodiments of the invention, in addition to electrical and chemical (i.e. drug) stimulation, other types of stimulations can also be used, for example, magnetic, thermal and/or ultrasonic stimulation can be used to modulate the targeted subcaudate area in a predetermined manner. Magnetic stimulation can be provided by internally implanted probes or by externally applied directed magnetic fields. Thermal stimulation can be provided by using implanted probes that are regulated to produce or emit heat and/or cold temperatures. An intraparenchymal catheter and a programmable pump coulob be used for such a purpose.

According to still another aspect of the present invention is a method for treating a patient with a neurological and/or schizophrenic disorder, comprising applying chronic electrical stimulation to at least a portion of subcaudate area of the brain of the patient under conditions effective to provide the patient with at least a partial relief from said neurological and/or schizophrenic disorder by means of an electrical signal generator and at least an implantable electrode having a proximal end coupled to the said signal generator and a stimulation end capable of applying said chronic electric stimulation, the said conditions being such that electrical stimulation results in at least one of a significant increase in neuronal activity in the subcaudate area as measured by functional magnetic resonance imaging and a change in metabolism as measured by Positron Emission Tomography (PET).

According to another aspect of the present invention is a method for treating a patient with neurological and/or psychiatric disorder, comprising applying electrical stimulation to at least a portion of the subcaudate area of the brain of the patient under conditions effective to provide the patient with at least a partial relief from at least one of neurological or psychiatric disorder by means of an electrical signal generator and at least an implantable electrode having a proximal end coupled to the said signal generator and a stimulation end capable of applying said chronic electrical stimulation, the said conditions including a voltage in the range from about 0.5 volt to about 12 volts, a pulse width in the range from about 60 µs to about 450 µs and a frequency in the range from about 50 Hz to about 200 Hz.

In aspects the neurological and/or psychiatric disorders of the invention are depression and schizophrenia.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

BRIEF DESCRIPTION OF THE DRAWINGS

The present invention will become more fully understood from the detailed description given herein and from the accompanying drawings, which are given by way of illustration only and do not limit the intended scope of the invention.

DETAILED DESCRIPTION OF THE INVENTION

Figure 1:
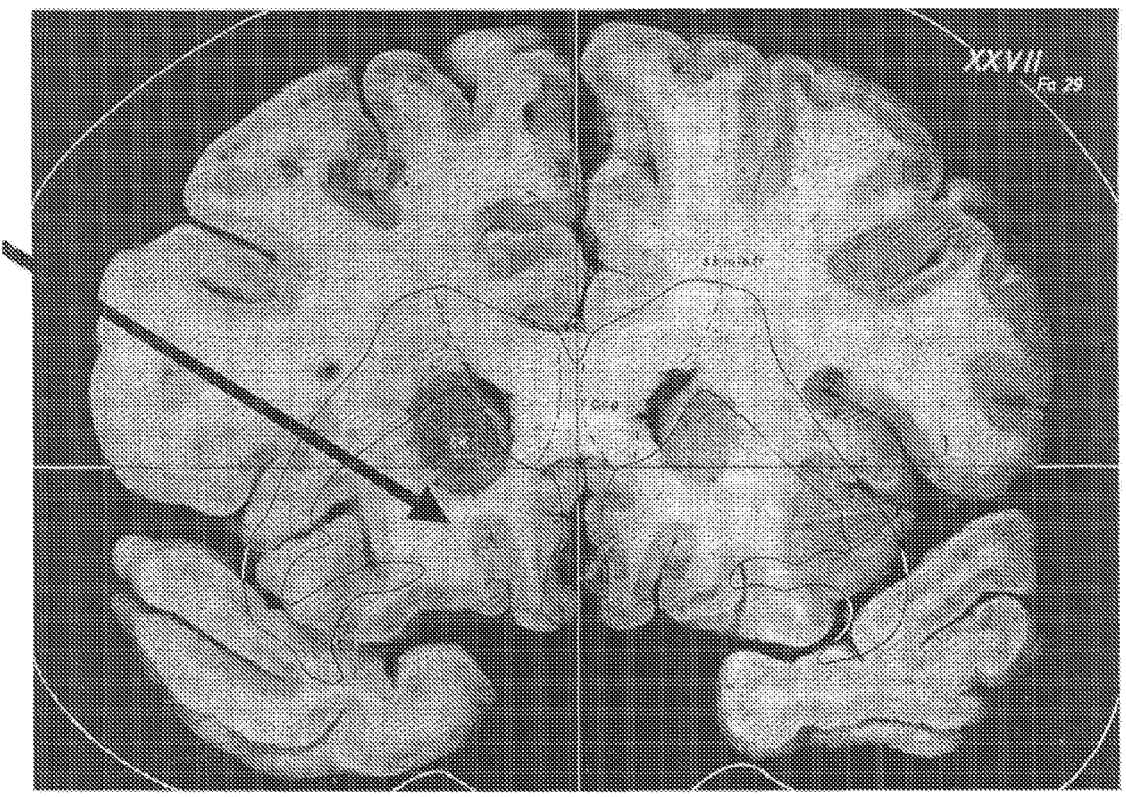
FIG. 1 is a coronal section of the human brain 29 mm anterior to the anterior commissure showing the caudate nucleus (Cd). The black arrow points to the subcaudate area white matter, the target for stimulation and/or drug infusion.
Figure 2:
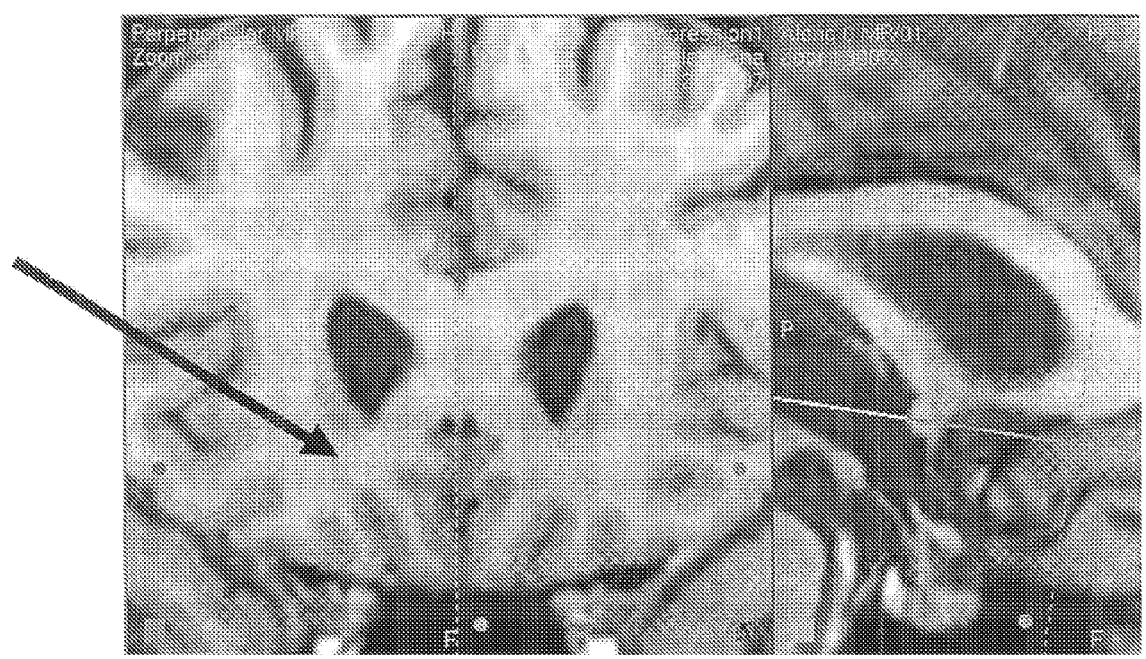
FIG. 2 is a coronal MRI showing the region of the subcaudate area shown with black arrow.
Figure 3:
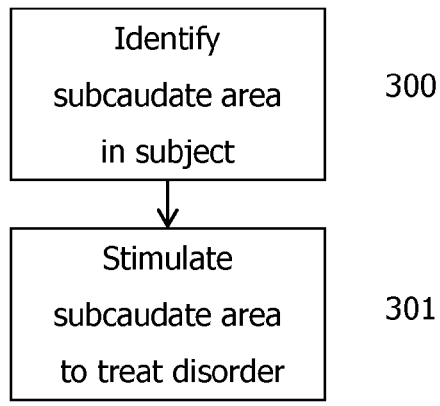
FIG. 3 shows a flowchart of an exemplary open loop method to treat a disorder as described herein.
Figure 4:
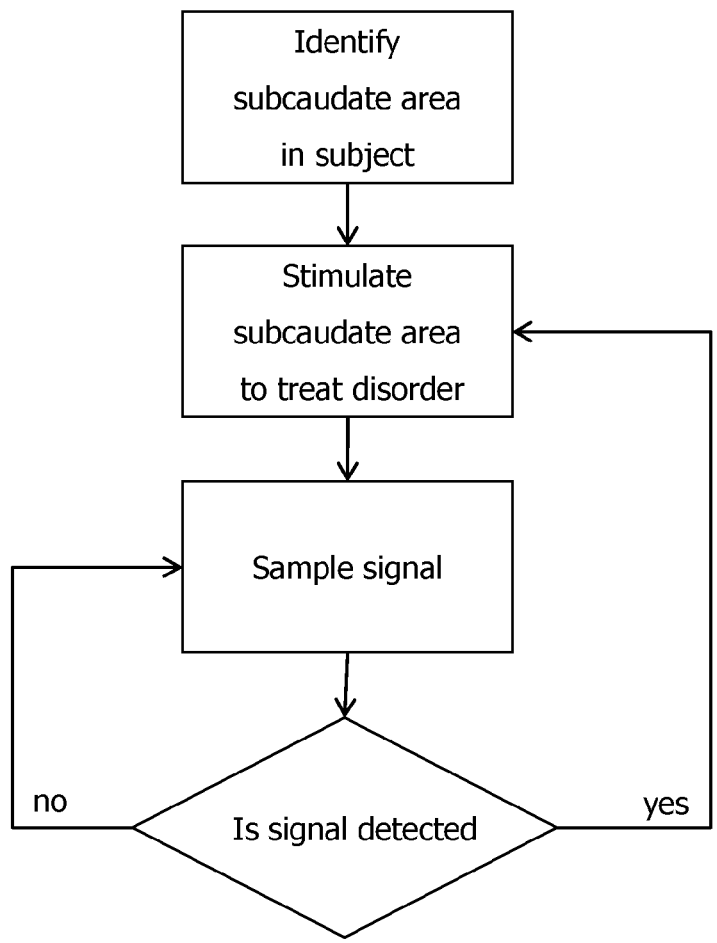
FIG. 4 shows a flowchart of an exemplary closed loop method to treat a disorder as described herein.

The present invention provides for the first time a method of treatment of the subcaudate white matter where abnormal neural activity in or coursing through this region leads to neurological and/or psychiatric disorders. The method of the invention comprises the use of deep tissue stimulation (DTS) and/or pharmacological infusion to this area. FIG. 1 is a coronal section of the human brain showing the caudate nucleus and FIG. 2 is a coronal MRI showing the region of the subcaudate area, below or ventral to the caudate nucleus to be the area of treatment in accordance with the present invention.

The various embodiments of the present invention provide reversible therapy to treat the various disorders. This reversibility has the advantage over known therapies for neurological disorders that are not reversible, in particular lesioning procedures. Reversibility allows the therapy to be discontinued if it proves ineffective or if it produces unwanted side effects. Reversibility also enables the performance of double-blind studies, which was not possible using the lesioning technique.

The tracks in the subcaudate area or region interconnect the thalamus, hypothalamus and the amygdala as well as cortical striatal and cortical striatal thalamic pathways. Fibers that may be influenced include the cortico-striatal projections, striatal projections, thalamocortical pathways as well as diagonal band of Broca and fibers crossing in the medial forebrain bundle and the anterior commissure. This means that simulation or the focal application of neuroactive substances here could influence the amygdala, the temporal lobe, the hippocampus, the orbitofrontal lobe and the entorhinal cortex, the cholinergic basal nuclei, as well as the hypothalamus. Further, the fibers crossing between the thalamus and frontal areas, particularly prefrontal and orbital frontal areas, would be expected to be influenced by stimulation in this area. This means that this target is in a position to influence cognitive, affective, circadian, endocrine sleep, depression, mood disorders, apathy, aggressive behavior, Attention deficit behavior, schizophrenia, pain, movement, judgment and cognition as well as learning and memory disorders.

In aspects of the invention neurological and psychiatric disorders for treatment would include major depression and also bi-polar disorders, but a number of other psychiatric disorders including Mood and Anxiety Disorders and disorders of Axis I including Schizophrenia, Catatonia and OCD would be likely to improve with modulation of this circuitry by either stimulation or the infusion of neuroactive substances to either drive underperforming circuits, or inhibit the activity of pathological circuits crossing through this area. Other disorders include sleep, attention disorders, apathy, pain, eating disorders, mood and anxiety disorders, cognitive and memory disorders, emotional disorders and disorders of learning and of higher mental processing.

The subcaudate area white matter procedure can be performed under local or general anesthesia. The targeting is done from standard MRI. The head of the caudate is identified and is well seen on a standard coronal slice. The white matter underlying the caudate nucleus can be readily identified with standard T1 or T2 MRI imaging (see FIGS. 1 and 2). In one aspect, a sequence is in the coronal plain and T2 imaging. The subcaudate white matter tracks can be identified as lying from approximately 15 to 35 mm to the anterior to the anterior commissural and from approximately 5-25 mm from the midline. The subcaudate nucleus ends at the vertical level of the intercommissural line or within about 10 mm below this line, and the corresponding subcaudate white matter would be thus between about 5 and 20 mm below the intercommissural line. The target is approximately 15 mm plus or minus 10 mm from the midline and lies approximately 10 mm plus or minus 10 mm below the intercommissural line and approximately 25 mm plus or minus 10 mm anterior to the anterior commissure. It is desirable to provide stimulating electrodes or an intraparenchymal catheter for the delivery of neuroactive pharmacological substances could be inserted at this level.

A variety of electrical stimulation systems can be used in the method of the invention to provide deep brain stimulation. Stimulation system generates and applies a stimulus to a target area of the brain or is in communication with the target area of the brain, the subcaudate white matter. In general, the stimulation system includes an implantable pulse generating source, such as an electrical stimulation source and an implantable stimulation portion, for example an electrode. In certain embodiments the electrode is comprised within an electrical stimulation lead. In operation, both of these primary components are implanted in the person's body. Stimulation source is coupled to a connecting portion of electrical stimulation lead. Stimulation source controls the electrical signals transmitted to electrodes located on a stimulating portion of electrical stimulation lead, located adjacent the target brain tissue, according to suitable signal parameters (e.g., duration, intensity, frequency, etc.). A doctor, the patient, or another user of stimulation source may directly or indirectly input signal parameters for controlling the nature of the electrical stimulation provided.

The stimulation source may include an implantable pulse generator (IPG). One of skill in the art is aware that any commercially available implantable pulse generator can be used in the present invention, as well as a modified version of any commercially available pulse generator. Thus, one of skill in the art would be able to modify an IPG to achieve the desired results. An exemplary IPG is one that is manufactured by Advanced Neuromodulation Systems, Inc. A doctor, the patient, or another user of stimulation source may use a controller located external to the person's body to provide control signals for operation of stimulation source. Controller provides the control signals to wireless transmitter, wireless transmitter transmits the control signals and power to the wireless receiver of stimulation source, and stimulation source uses the control signals to vary the signal parameters of electrical signals transmitted through electrical stimulation lead to the stimulation site. An example wireless transmitter may be one manufactured by Advanced Neuromodulation Systems, Inc., such as the Renew™ System.

The system or device used in the present invention may include but not be limited to those described in U.S. Pat. Nos. 4,692,147, 5,193,539, 5,193,540, 5,312,439, 5,324,316, 5,405,367, 6,051,017 6,735,475; 6,735,474 and 6,782,292 and in WO 98/37926, WO 98/43700 and WO 98/43701 (the disclosures of which are incorporated herein by reference in their entirety).

Electrical stimulation of the subcaudate area white matter may be implemented by providing pulses to the electrodes having amplitudes of about 0.1 to about 20 volts, pulse widths varying from about 0.02 to about 500 microseconds, and frequencies varying from about 1 to about 2500 Hz. The appropriate stimulation pulses are generated by device as programmed. The type of stimulation administered by device to the brain depends on the specific location at which the electrodes of tube are surgically implanted. These stimulations can be provided at multiple sites as described herein. That is, they can be provided simultaneously to more than one site, or sequentially as required or a combination of both. The stimulation be provided pre-programmed on a daily basis or patient activated or on a closed feedback system in response to a physiological parameter.

A microprocessor within the device implemented to provide the stimulus is programmed so that the desired stimulation can be delivered to the specific brain sites described. Alternatively, the patient may control the stimulation manually.

The method of the invention can use a combination of electrical stimulation and infusion of a drug (pharmacological substance). Infusion and electrical stimulation may be provided as a combined catheter and electrode and can be applied separately or simultaneously and repeated as required/desired. The device may take the form of a device shown in U.S. Pat. No. 4,692,147 (the contents of which is incorporated by reference).

Such combination of electrical and pharmacological agent may increase the effectiveness of the electrical stimulation method of the present invention, and thus it may be desirable to combine electrical stimulation with chemical stimulation to treat the neurological and schizophrenic disorder. For example, infusion alone can be applied from a certain time, infusion and stimulation can both be applied from a different time, and stimulation alone can be applied from yet a different time to the first two. This is understood to be determined by the medical practitioner for the patient as is understood by one of skill in the art. In addition to electrical and chemical stimulation, other types of stimulations can also be used, for example, magnetic, thermal and/or ultrasonic stimulation can be used. Magnetic stimulation can be provided by internally implanted probes or by externally applied directed magnetic fields, for example, U.S. Pat. Nos. 6,592,509; 6,132,361; 5,752,911; and 6,425,852, (each of which is incorporated herein in its entirety). Thermal stimulation can be provided by using implanted probes that are regulated for heat and/or cold temperatures which can stimulate or inhibit neuronal activity, for example, U.S. Pat. No. 6,567,696 (incorporated herein by reference in its entirety).

The electrical stimulation might be applied intermittently to a background of continuous or modulated infusion of one or more drugs. Still another approach would be to alternate the application of electrical stimulation and drug infusion. This method advantageously may reduce the risk of damaging one population of neurons through overactivation. Electrical stimulation or drug infusions may be alternatively delivered to multiple sites in the brain as desired.

The present invention may be implemented by providing different drug dosages from about a zero dosage to about a 1.0 ml dosage with about 0.1 ml increments between choices. One of skill in the art could determine suitable dosages. The time interval between dosages can be selected between one and twelve hours in seven choices. The selected dosage and interval of a drug is then delivered to the portions of the brain identified as being involved in hunger and satiety; palatability and aversion; hedonism; reward/addiction behaviour; mood; anxiety; depression; taste; and smell.

Suitable drugs for use in the present invention excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium; Mestinon; trazodone; SSRIs (e.g., flouxetine, paroxetine, sertraline, citalopram and fluvoxamine); tricyclic antidepressants (e.g., imipramine, amitriptyline, doxepin, desipramine, trimipramine and nortriptyline), monoamine oxidase inhibitors (e.g., phenelzine, tranylcypromine, isocarboxasid)), generally have an excitatory effect on neural tissue, while inhibitory neurotransmitters (e.g., dopamine, glycine, and gamma-aminobutyric acid (GABA)), agonists thereof, and agents that act to increase levels of an inhibitory neurotransmitter(s) generally have an inhibitory effect (e.g., benzodiasepine (e.g., chlordiazepoxide, clonazepam, diazepam, lorazepam, oxazepam, prazepam alprazolam); flurazepam, temazepam, or triazolam). (Dopamine acts as an excitatory neurotransmitter in some locations and circumstances, and as an inhibitory neurotransmitter in other locations and circumstances.) However, antagonists of inhibitory neurotransmitters (e.g., biculline) and agents that act to decrease levels of an inhibitory neurotransmitter(s) have been demonstrated to excite neural tissue, leading to increased neural activity. Similarly, excitatory neurotransmitter antagonists (e.g., prazosin, and metoprolol) and agents that decrease levels of excitatory neurotransmitters may inhibit neural activity. Yet further, lithium salts and anesthetics (e.g., lidocane) may also be used in combination with electrical stimulation.

The methods of therapy of the present invention may be delivered in a closed loop or open loop fashion. In the closed loop iteration, the electrical or focal drug delivery is dependent of detection of a signal or a physical, electrical value within range. In the responsive mode, the signal is detected, the therapeutic intervention is administered on a contigent basis, the signal is re-sampled and ongoing delivery or scessation of stimulation or drug delivery is determined by whether the signal now detected in within the desired value or range. This closed loop mode includes signal detection, analysis, and therapeutic command and delivery. This is done within a single self contained fully implantable device.

Delivery of the drugs to the specific target locations of the subcaudate white matter described supra will result in the fewest neurological side effects since the effects of the drugs on other neurons subserving other functions is minimized. Exemplary drugs with their ranges of dosages and drug concentrations for some of the classes of drugs are identified in the following list: Adrenergic Agonist Clonidine HCL 10 nM-50 mµM Ephedrine HCL 10 nM-50 mµM Norepinephrine 10 nM-50 mµM Adrenergic Antagonists Verapamil HCL 10 nM-50 mµM Propranolol 10 nM-50 mµM Urapidil HCL 10 nM-50 mµM Opioid Agonist Morphine 0.1-500 mµM Opioid Antagonist Naloxone 0.1-500 mµM Serotonin Agonist Buspirone HCL 10 nM-50 mµM L-methyl serotonin 10 nM-50 mµM Serotonin Antagonist (−) Sulpiride 0.05-1 mµM spiperone HCL 0.1-10 mµM Propranolol HCL 0.05-1 mµM Pancreatic Polypeptide NPY 20-300 picoM Agonist PYY 2 picoM to 10 mµM Pancreatic Polypeptide Leptin 2 picoM to 10 mµM Antagonist GABA Agonists baclofen 0.1-10 mµM muscinol HBr 100-500 mµM GABA Antagonists Gabazine 1-50 mµM Saclofen 0.5-25 mµM Bicuulline 1-100 mµM picrotoxin 10-100 mµM Dopamine Antagonist (+) apomorphone HCL 5-20 mµM spiperone HCL 0.1-10 mµM haloperidol 10-100 mµM (−) Sulpiride 0.05-1 mµM *Dopamine Agonist methanesulfonate* 1-10 mµM Dopamine Agonist (−) apomorphine 10-30 mµM (cont.) pergolide Glucagon Agonist GLP-10.05-500 mµM Glucagon Antagonist exendin (9-39) 0.01-500 mµM Anesthetic Lidocaine hydrochloride 5-20 mµM.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Patients will be selected by committee for neurosurgical interventions for psychiatric disorders and very strict selection criteria. All patients must fulfill the criteria for schizophrenia or depression according to the Diagnostic and statistical manual of psychiatric disorders. The interventions and clinical evaluations will be performed at Toronto Western Hospital.

The invention claimed is:

1. A method for the treatment of neurological/psychiatric disorders in a patient, the method comprising administration of a stimulation selected from the group consisting of electrical, pharmacological, magnetic stimulation, thermal, ultrasonic and combinations thereof such that the stimulation is delivered to the subcaudate area approximately 15 mm to approximately 35 mm anterior to the anterior commissure, 15 mm or greater from the midline and approximately 5 mm to approximately 20 mm below the intercommissural line of said patient for a time, duration and frequency to decrease or substantially ameliorate the neurological/psychiatric disorder, wherein the neurological/psychiatric disorder is selected from the group consisting of major depression, bi-polar disorders, schizophrenia, catatonia and obsessive compulsive disorder.

2. The method of claim 1, wherein said neurological/psychiatric disorder is Schizophrenia.

3. The method of claim 1, wherein said stimulation is applied to white matter of the subcaudate nucleus.

4. The method of claim 3, wherein said stimulation affects tracks in the subcaudate region.

5. The method of claim 4, wherein said stimulation modulates neural activity in affected circuitry to improve neurological and/or psychiatric function.

6. The method of claim 1, wherein said electrical stimulation may be implemented by providing pulses to electrodes targeting areas of said brain, said pulses having amplitudes of about 0.1 to about 20 volts, pulse widths varying from about 0.02 to about 500 microseconds, and frequencies varying from about 1 to about 2500 Hz.

7. The method of claim 1, wherein said method comprises the use of one or more pharmacological agents concurrently with a selected stimulation and/or following a selected stimulation.

8. The method of claim 7, wherein said method comprises combinations of electrical stimulation and infusion of pharmacological agents.

9. The method of claim 8, wherein said stimulation is provided in one or more of the following:
a) intermittently,
b) intermittently with concurrent continuous pharmacological agent infusion;
c) alternating with pharmacological agent infusion;
d) simultaneously to one or more selected areas;
e) sequentially to one or more areas; and
f) a combination of d) and e).

10. The method of claim 9, wherein said stimulation is provided in closed loop mode depending on the detection of a predetermined signal within a defined range of values.

11. The method of claim 10, wherein said stimulation is provided in a responsive mode with repeated sampling and redetection and redosing as required until the value of the detected signal lies within a specified range.

12. A method for treatment of mood and/or anxiety disorders in a patient, the method comprising administration of a stimulation selected from the group consisting of electrical, pharmacological, magnetic, thermal, ultrasonic and combinations thereof such that the stimulation is delivered to the subcaudate area approximately 15 mm to approximately 35 mm anterior to the anterior commissure, 15 mm or greater from the midline and approximately 5 mm to approximately 20 mm below the intercommissural line of said patient for a time, duration and frequency to decrease or substantially ameliorate the mood and/or anxiety disorder.

13. The method of claim 12 wherein the mood and/or anxiety disorder is depression.

14. The method of claim 12 wherein the mood and/or anxiety disorder can be associated with a disorder selected from the group consisting of cognitive, circadian, endocrine sleep, apathy, aggressive behavior, attention deficit behavior, pain, movement, judgment and cognition, learning and memory disorders and a combination thereof and the stimulation improves the disorder associated with the mood and/or anxiety disorder.

15. A method of treating a mood or anxiety disorder in a patient comprising:
positioning a stimulation lead within the patient such that at least one electrode of the lead is positioned in or in direct contact with the subcaudate area approximately 15 mm to approximately 35 mm anterior to the anterior commissure, 15 mm or greater from the midline and approximately 5 mm to approximately 20 mm below the intercommissural line;
generating electrical pulses using a pulse generator to apply electrical pulses to stimulate the subcaudate area of the patient utilizing the at least one electrode of the stimulation lead, wherein the applying the electrical pulses effectively treats the mood or anxiety disorder of the patient.

* * * * *